United States Patent [19]

Weber

[11] 4,396,548
[45] Aug. 2, 1983

[54] PYRAZOLINE DERIVATIVES

[75] Inventor: Kurt Weber, Basel, Switzerland

[73] Assignee: Ciba-Geigy Corporation, Ardsley, N.Y.

[21] Appl. No.: 162,343

[22] Filed: Jun. 23, 1980

Related U.S. Application Data

[63] Continuation of Ser. No. 917,448, Jun. 21, 1978, abandoned.

[30] Foreign Application Priority Data

Jun. 27, 1977 [LU] Luxembourg .................. 77629

[51] Int. Cl.³ .......................................... C07D 231/06
[52] U.S. Cl. ............................ 260/239.65; 260/239.7; 260/239.8; 260/239.9; 260/301.27; 260/100
[58] Field of Search ............. 260/239.65, 239.7, 239.8, 260/239.9

[56] References Cited

U.S. PATENT DOCUMENTS

| | | | |
|---|---|---|---|
| 3,131,079 | 4/1964 | Wagner et al. | 260/239.7 |
| 3,135,742 | 6/1964 | Wagner et al. | 260/239.9 |
| 3,598,810 | 8/1971 | Troxler et al. | 260/239.7 |
| 3,674,714 | 7/1972 | Troxler et al. | 260/239.7 |
| 3,789,056 | 1/1974 | Pfirrman | 260/239.9 |
| 3,836,522 | 9/1974 | Somlo et al. | 260/239.9 |
| 3,865,816 | 2/1975 | Mengler et al. | 260/239.9 |
| 3,925,367 | 12/1975 | Boehmke et al. | 260/239.65 |
| 4,263,431 | 4/1981 | Weber et al. | 542/459 |

FOREIGN PATENT DOCUMENTS

| | | |
|---|---|---|
| 1080963 | 5/1960 | Fed. Rep. of Germany . |
| 1155418 | 10/1963 | Fed. Rep. of Germany . |
| 2050725 | 4/1972 | Fed. Rep. of Germany . |
| 1350502 | 4/1974 | United Kingdom . |
| 1404037 | 8/1975 | United Kingdom . |

Primary Examiner—Henry R. Jiles
Assistant Examiner—Natalia Harkaway
Attorney, Agent, or Firm—Edward McC. Roberts

[57] ABSTRACT

Pyrazoline derivatives of the formula

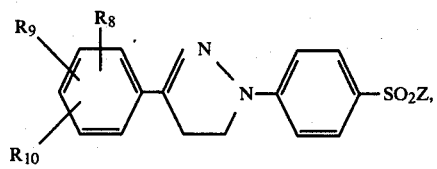

wherein Z represents a radical of the formula

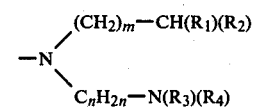

or of the formula

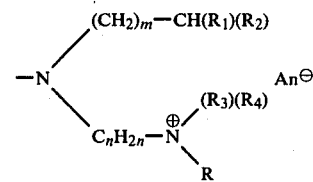

and R, $R_1$, $R_2$, $R_3$, $R_4$, $R_8$, $R_9$ and $R_{10}$ represent specific substituents and $An^\ominus$ represents the equivalent of a colorless anion, a process for the production of these compounds and their use as fluorescent brightening agents.

3 Claims, No Drawings

PYRAZOLINE DERIVATIVES

This is a Cont. of application Ser. No. 917,448 filed on June 21, 1978 now abandoned.

The present invention relates to novel pyrazoline derivatives, a process for their production and to the use thereof for the fluorescent brightening of organic materials.

1,3-Diarylpyrazoline derivatives which contain in the 1-position a sulphamoyl group at the aryl radical and which can be used for brightening organic material are known from the literature (cf. for example German Pat. Nos. 1,080,963 and 1,155,418, German Offenlegungsschrift No. 2,050,725 and U.S. Pat. Nos. 3,598,810 and 3,674,714).

The invention relates to novel pyrazoline derivatives of the formula

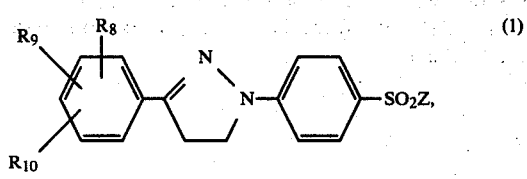

wherein $R_8$, $R_9$ and $R_{10}$, each independently of the other, represent hydrogen, halogen, lower alkyl or lower alkoxy, and Z represents a radical of the formula

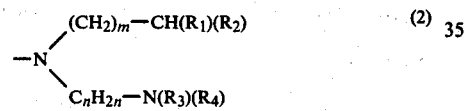

wherein $R_1$ represents hydrogen or lower alkyl, $R_2$ represents cyano, $-COR_5$, $-COOR_5'$ or $-CONR_6R_7$, wherein $R_5$ represents alkyl of 1 to 3 carbon atoms, $R_5'$ represents lower alkyl which is unsubstituted or substituted by hydroxyl, lower alkoxy, phenoxy, tolyloxy or phenyl, and $R_6$ and $R_7$, each independently of the other, represent hydrogen, lower alkyl, lower hydroxyalkyl, or together with the nitrogen atom to which they are attached, represent a saturated heterocyclic ring, $R_3$ and $R_4$, each independently of the other, represent lower alkyl, lower hydroxyalkyl, or together with the nitrogen atom to which they are attached represent a saturated heterocyclic ring, m is 0 or 1, and n is an integer from 2 to 6, or of the formula

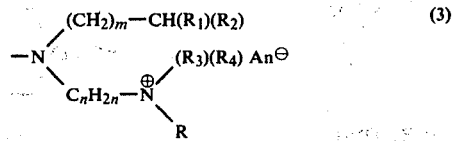

wherein

R represents hydrogen, allyl or lower alkyl which is unsubstituted or substituted by hydroxyl, cyano, lower alkoxy, carbamoyl, lower alkoxycarbonyl, phenyl, phenoxy or tolyloxy, $An^\ominus$ represents the equivalent of a colourless anion, and $R_1$, $R_2$, $R_3$, $R_4$, m and n are as defined in formula (2).

In the compounds of the formula (1), wherein Z represents the radical of the formula (3), the anion can be replaced by another anion by methods which are in themselves known [cf. for example Houben-Weyl "Methoden der Organischen Chemie", Vol. XI/2 (4th edition, 1958), page 620 ff.]. Thus, for example, the compound can be dissolved in water or in an aqueous organic medium and treated with a silver salt (e.g. silver nitrate or silver acetate) if a halogen anion ($Cl^\ominus$, $Br^\ominus$, $I^\ominus$) is to be replaced by another anion (e.g. a nitrate or acetate ion), or with a barium salt if, instead of a sulphate ion, another anion is to be introduced. This exchange can be carried out in one or more steps, for example via the carbonate or the hydroxide, or also with the aid of ion exchangers. Halogen ions, especially chlorine ions, can be converted into salts of lower aliphatic carboxylic acids if they are reacted in aqueous or anhydrous medium with lower aliphatic carboxylic acids and an epoxide compound containing not more than 12 carbon atoms (cf. French Pat. No. 2,290,479).

Preferred pyrazoline derivatives are those of the formula

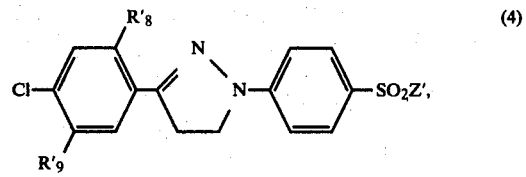

wherein $R_8'$ represents hydrogen or lower alkyl, $R_9'$ represents hydrogen or chlorine, and $Z'$ represents a radical of the formula

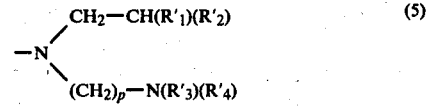

wherein $R_1'$ represents hydrogen or methyl, $R_2'$ represents cyano or $-CONR_6'R_7'$, wherein $R_6'$ and $R_7'$, each independently of the other, represent hydrogen, lower alkyl, lower hydroxyalkyl, or together with the nitrogen atom to which they are attached represent a pyrrolidine, piperidine or morpholine ring, $R_3'$ and $R_4'$ represent lower alkyl, lower hydroxyalkyl, or together with the nitrogen atom to which they are attached represent a pyrrolidine, piperidine, morpholine or thiomorpholine ring, and P is 2 or 3, or of the formula

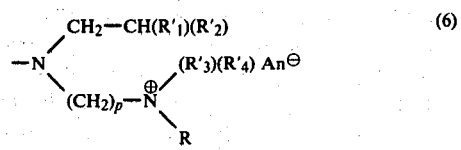

wherein

R represents hydrogen, allyl or lower alkyl which is unsubstituted or substituted by hydroxyl, cyano, lower alkoxy, carbamoyl, lower alkoxycarbonyl, phenyl, phenoxy or tolyloxy, An$^\ominus$ represents the equivalent of a colourless anion, and $R_1'$, $R_2'$, $R_3'$, $R_4'$ and p are as defined in formula (5).

Pyrazoline derivatives having a particularly interesting utility are those of the formula

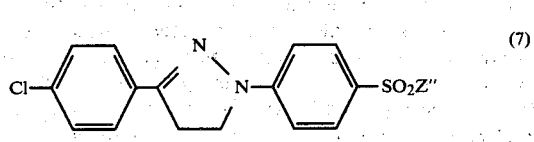 (7)

wherein Z" represents a radical of the formula

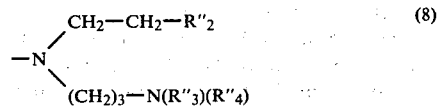 (8)

wherein
$R_2''$ represents cyano or —CONH$_2$,
$R_3''$ represents lower alkyl, and
$R_4''$ represents lower alkyl,
or of the formula

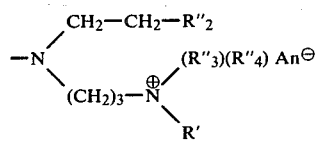 (9)

wherein
R' represents hydrogen, lower alkyl or lower hydroxyalkyl, and

An$^\ominus$ represents the equivalent of a colourless anion, and $R_2''$, $R_3''$ and $R_4''$ are as defined in formula (8).

Suitable alkyl radicals R and $R_1$ to $R_7$ are those containing 1 to 18, preferably 1 to 4, carbon atoms. The term "lower" denotes that an alkyl or alkoxy radical contains 1 to 4 carbon atoms.

Suitable colourless anions An$^\ominus$ in the formulae (3), (6) and (9) are for example both organic or inorganic ions, such as the formiate, acetate, chloroacetate, propionate, oxalate, lactate, tartrate, benzoate, maleinate ions, or the chloride, bromide, iodide, perchlorate, methyl sulphate, sulphate, bisulphate, benzenesulphonate, 4-methylbenzenesulphonate, 4-chlorobenzenesulphonate ions. Water-soluble double salt compounds with inorganic salts, such as zinc chloride, are also possible. If in compounds of the formula (1) Z represents a radical of the formula (3), wherein R represents hydrogen (i.e. if the compounds are acid adducts), then An$^\ominus$ is preferably an acetate, formiate, chloride or bisulphate ion. The pyrazoline derivatives of the formula (1) can be obtained in a manner which is in itself known, for example by reaction of a pyrazolinesulphonic acid derivative of the formula

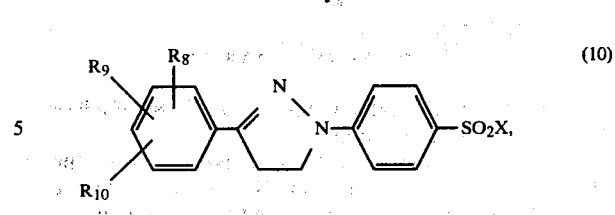 (10)

wherein X represents halogen and $R_8$, $R_9$ and $R_{10}$ have the above meanings, with an amine of the formula

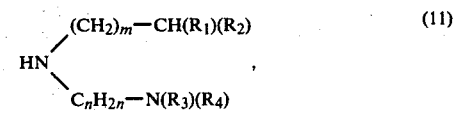 (11)

wherein $R_1$, $R_2$, $R_3$, $R_4$, m and n have the above meanings, and optionally reacting the resulting reaction product with an acid or a quaternising agent.

Amines of the formula (11) are for example those of the formula

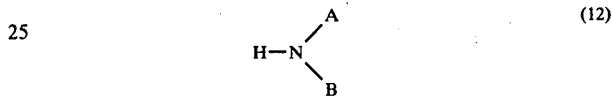 (12)

wherein A and B have the meanings given in Table I.

TABLE I

| A | B |
|---|---|
| —CH$_2$CH$_2$CN | —C$_3$H$_6$N(CH$_3$)$_2$ |
| —CH$_2$CH$_2$CN | —C$_3$H$_6$N(C$_2$H$_5$)$_2$ |
| —CH$_2$CH$_2$CN | —C$_3$H$_6$N(C$_4$H$_9$)$_2$ |
| —CH$_2$CH$_2$CN | —C$_3$H$_6$N⟨O⟩ (morpholino) |
| —CH$_2$CH$_2$CN | —C$_3$H$_6$N⟨ ⟩ (piperidino) |
| —CH$_2$CH$_2$CN | —C$_3$H$_6$N(C$_2$H$_5$)(CH$_3$) |
| —CH$_2$CH$_2$CN | —C$_3$H$_6$N(CH$_2$CH$_2$OH)$_2$ |
| —CH$_2$CONH$_2$ | —C$_3$H$_6$N(CH$_3$)$_2$ |
| —CH$_2$CONH$_2$ | —C$_3$H$_6$N(C$_2$H$_5$)$_2$ |
| —CH$_2$CONH$_2$ | —C$_3$H$_6$N(C$_4$H$_9$)$_2$ |
| —CH$_2$CONH$_2$ | —C$_3$H$_6$N⟨O⟩ (morpholino) |
| —CH$_2$CONH$_2$ | —C$_3$H$_6$N⟨ ⟩ (piperidino) |
| —CH$_2$CONH$_2$ | —C$_3$H$_6$N(C$_2$H$_5$)(CH$_3$) |

TABLE I-continued

| A | B |
|---|---|
| —CH₂CONH₂ | —C₃H₆N(CH₂CH₂OH)₂ |
| —CH₂CH₂CONH₂ | —C₃H₆N(CH₃)₂ |
| —CH₂CH₂CONH₂ | —C₃H₆N(C₂H₅)₂ |
| —CH₂CH₂CONH₂ | —C₃H₆N(C₄H₉)₂ |
| —CH₂CH₂CONH₂ | —C₃H₆N⟨morpholino⟩ (—C₃H₆N O) |
| —CH₂CH₂CONH₂ | —C₃H₆N⟨piperidino⟩ |
| —CH₂CH₂CONH₂ | —C₃H₆N(C₂H₅)(CH₃) |
| —CH₂CH₂CONH₂ | —C₃H₆N(CH₂CH₂OH)₂ |
| —CH₂CH₂CON(CH₃)₂ | —C₃H₆N(CH₃)₂ |
| —CH₂CH₂CON(CH₃)₂ | —C₃H₆N(C₂H₅)₂ |
| —CH₂CH₂CON(CH₃)₂ | —C₃H₆N(C₄H₉)₂ |
| —CH₂CH₂CON(CH₃)₂ | —C₃H₆N⟨morpholino⟩ |
| —CH₂CH₂CON(CH₃)₂ | —C₃H₆N⟨piperidino⟩ |
| —CH₂CH₂CON(CH₃)₂ | —C₃H₆N(C₂H₅)(CH₃) |
| —CH₂CH₂CON(CH₃)₂ | —C₃H₆N(CH₂CH₂OH)₂ |
| —CH₂CH₂CON(C₂H₅)₂ | —C₃H₆N(CH₃)₂ |
| —CH₂CH₂CON(C₂H₅)₂ | —C₃H₆N(C₂H₅)₂ |
| —CH₂CH₂CON(C₂H₅)₂ | —C₃H₆N(C₄H₉)₂ |
| —CH₂CH₂CON(C₂H₅)₂ | —C₃H₆N⟨morpholino⟩ |
| —CH₂CH₂CON(C₂H₅)₂ | —C₃H₆N⟨piperidino⟩ |
| —CH₂CH₂CON(C₂H₅)₂ | —C₃H₆N(C₂H₅)(CH₃) |
| —CH₂CH₂CON(C₂H₅)₂ | —C₃H₆N(CH₂CH₂OH)₂ |
| —CH₂CH₂CON⟨morpholino⟩ | —C₃H₆N(CH₃)₂ |
| —CH₂CH₂CON⟨morpholino⟩ | —C₃H₆N(C₂H₅)₂ |
| —CH₂CH₂CON⟨morpholino⟩ | —C₃H₆N(C₄H₉)₂ |
| —CH₂CH₂CON⟨morpholino⟩ | —C₃H₆N⟨morpholino⟩ |
| —CH₂CH₂CON⟨morpholino⟩ | —C₃H₆N⟨piperidino⟩ |
| —CH₂CH₂CON⟨morpholino⟩ | —C₃H₆N(C₂H₅)(CH₃) |
| —CH₂CH₂CON⟨morpholino⟩ | —C₃H₆N(CH₂CH₂OH)₂ |
| —CH₂CH₂COOCH₃ | —C₃H₆N(CH₃)₂ |
| —CH₂CH₂COOCH₃ | —C₃H₆N(C₂H₅)₂ |
| —CH₂CH₂COOCH₃ | —C₃H₆N(C₄H₉)₂ |
| —CH₂CH₂COOCH₃ | —C₃H₆N⟨morpholino⟩ |
| —CH₂CH₂COOCH₃ | —C₃H₆N⟨piperidino⟩ |
| —CH₂CH₂COOCH₃ | —C₃H₆N(C₂H₅)(CH₃) |
| —CH₂CH₂COOCH₃ | —C₃H₆N(CH₂CH₂OH)₂ |
| —CH₂CH₂COOC₂H₅ | —C₃H₆N(CH₃)₂ |
| —CH₂CH₂COOC₂H₅ | —C₃H₆N(C₂H₅)₂ |
| —CH₂CH₂COOC₂H₅ | —C₃H₆N(C₄H₉)₂ |
| —CH₂CH₂COOC₂H₅ | —C₃H₆N⟨morpholino⟩ |
| —CH₂CH₂COOC₂H₅ | —C₃H₆N⟨piperidino⟩ |
| —CH₂CH₂COOC₂H₅ | —C₃H₆N(C₂H₅)(CH₃) |
| —CH₂CH₂COOC₂H₅ | —C₃H₆N(CH₂CH₂OH)₂ |
| —CH₂CH₂COOCH₂CH₂OH | —C₃H₆N(CH₃)₂ |
| —CH₂CH₂COOCH₂CH₂OH | —C₃H₆N(C₂H₅)₂ |
| —CH₂CH₂COOCH₂CH₂OH | —C₃H₆N(C₄H₉)₂ |

TABLE I-continued

| A | B |
|---|---|
| —$CH_2CH_2COOCH_2CH_2OH$ | —$C_3H_6N$⟨O⟩ (morpholino) |
| —$CH_2CH_2COOCH_2CH_2OH$ | —$C_3H_6N$⟨ ⟩ (piperidino) |
| —$CH_2CH_2COOCH_2CH_2OH$ | —$C_3H_6N(C_2H_5)(CH_3)$ |
| —$CH_2CH_2COOCH_2CH_2OH$ | —$C_3H_6N(CH_2CH_2OH)_2$ |
| —$CH_2CH_2COOCH_2CH_2OCH_3$ | —$C_3H_6N(CH_3)_2$ |
| —$CH_2CH_2COOCH_2CH_2OCH_3$ | —$C_3H_6N(C_2H_5)_2$ |
| —$CH_2CH_2COOCH_2CH_2OCH_3$ | —$C_3H_6N(C_4H_9)_2$ |
| —$CH_2CH_2COOCH_2CH_2OCH_3$ | —$C_3H_6N$⟨O⟩ (morpholino) |
| —$CH_2CH_2COOCH_2CH_2OCH_3$ | —$C_3H_6N$⟨ ⟩ (piperidino) |
| —$CH_2CH_2COOCH_2CH_2OCH_3$ | —$C_3H_6N(C_2H_5)(CH_3)$ |
| —$CH_2CH_2COOCH_2CH_2OCH_3$ | —$C_3H_6N(CH_2CH_2OH)_2$ |
| —$CH_2CH_2COCH_3$ | —$C_3H_6N(CH_3)_2$ |
| —$CH_2CH_2COCH_3$ | —$C_3H_6N(C_2H_5)_2$ |
| —$CH_2CH_2COCH_3$ | —$C_3H_6N(C_4H_9)_2$ |
| —$CH_2CH_2COCH_3$ | —$C_3H_6N$⟨O⟩ (morpholino) |
| —$CH_2CH_2COCH_3$ | —$C_3H_6N$⟨ ⟩ (piperidino) |
| —$CH_2CH_2COCH_3$ | —$C_3H_6N(C_2H_5)(CH_3)$ |
| —$CH_2CH_2COCH_3$ | —$C_3H_6N(CH_2CH_2OH)_2$ |
| —$CH_2CH_2CN$ | —$C_2H_4$—N⟨ ⟩ (pyrrolidino) |

The amines of the formula (11), for example the preferred amines listed in Table II, are obtained by methods which are in themselves known, for example as described in German Offenlegungsschrift 2,060,085.

TABLE II

| Amine | Acrylic acid derivative | Adduct (Amine of formula (11)) |
|---|---|---|
| $(C_2H_5)_2N$—$(CH_2)_3$—$NH_2$ | $CH_2$=$CH$—$CN$ | $(C_2H_5)_2N$—$(CH_2)_3$—$NH$—$CH_2$—$CH_2$—$CN$ |
| $(HO$—$CH_2$—$CH_2)_2N$—$(CH_2)_3NH_2$ | $CH_2$=$CH$—$CO$—$NH_2$ | $(HO$—$CH_2$—$CH_2)_2N$—$(CH_2)_3$—$NH$—$CH_2$—$CH_2$—$CO$—$NH_2$ |
| $(C_2H_5)_2N$—$CH_2CH_2$—$NH_2$ | $CH_2$=$CH$—$CN$ | $(C_2H_5)_2N$—$CH_2CH_2$—$NH$—$CH_2$—$CH_2$—$CN$ |
| piperidino-$(CH_2)_3$—$NH_2$ | $CH_2$=$CH$—$CN$ | piperidino-$(CH_2)_3$—$NH$—$CH_2$—$CH_2$—$CN$ |

| Amine | Acrylic acid derivative | Adduct |
|---|---|---|
| morpholino-$(CH_2)_3$—$NH_2$ | $CH_2$=$CH$—$CN$ | morpholino-$(CH_2)_3$—$NH$—$CH_2$—$CH_2$—$CN$ |

TABLE II-continued

| | | |
|---|---|---|
| 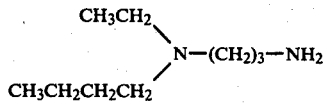 | CH₂=CH—CN | 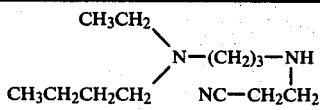 |
| 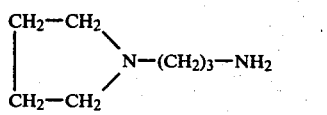 | CH₂=CH—CN | 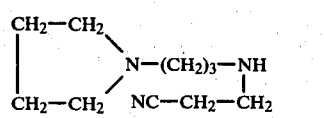 |
| 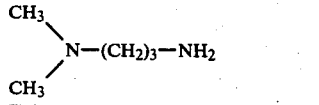 | CH₂=CH—CN | 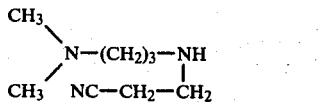 |

Suitable quaternising agents are for example esters of sulphuric acid, such as dimethyl sulphate or diethyl sulphate, or the esters of aromatic or aliphatic sulphonic acids, such as the methyl, ethyl or n-butyl esters of benzenesulphonic acid, 4-methylbenzenesulphonic acid or 4-chlorobenzenesulphonic acid, the methyl or ethyl esters of methanesulphonic acid, ethanesulphonic acid, 1-propane- or 2-propanesulphonic acid. Suitable alkylating agents are also alkyl and aralkyl halides, such as methyl chloride, methyl bromide, ethyl bromide, n-butyl bromide, benzyl chloride, benzyl bromide and allyl chloride. It is also possible to use as alkylating agents alkyl halides containing 1 to 5 carbon atoms, which are substituted by hydroxyl, alkoxy, phenoxy, cresoxy, carbalkoxy, cyano or preferably by aminocarbonyl groups, such as 2-chloroethanol or 2-bromomethanol, 2-methoxy-, 2-ethoxy-, 2-n-butoxy-, 2-phenoxy- or 2-para-cresoxyethyl chloride or bromide, chloroacetonitrile, and preferably chloro- or bromoacetamide or ethyl chloro- or bromoacetate or β-chloropropionamide. Finally, suitable alkylating agents are also ethylene oxide, 1,2-propylene oxide, 1,2-butylene oxide, glycide, methoxyethylene oxide, styrene oxide, phenyl glycidyl ether or epichlorohydrin in the presence of suitable acids, for example formic or lactic acid and especially acetic acid. The quaternisation can be carried out in aqueous, aqueous-organic or organic suspension or solution at temperatures between 0° and 160° C., preferably between 20° and 130° C. At least 1 mole of the quaternising agent must be used for each tertiary amino group to be quaternised. When using volatile quaternising agents such as methylene chloride, methyl bromide, ethyl bromide, it is advantageous to carry out the reaction in a pressure vessel.

Suitable solvents in which the quaternisation can be carried out are in general all inert solvents. Preferred solvents are those which dissolve the starting material and from which the end product immediately precipitates. Examples of such solvents are: aromatic hydrocarbons, such as benzene, toluene and xylene; halogenated hydrocarbons, such as methylene dichloride, trichloroethane, tetrachloroethylene, chlorobenzene or dichlorobenzene, also nitrobenzene, alkanols and open-chain or cyclic ethers, such as ethanol, isopropanol, butanol, diethyl ether, dibutyl ether, ethylene glycol monomethyl ether, ethylene glycol monoethyl ether, tetrahydrofurane, anisole or dioxane; ketones, such as acetone, cyclohexanone or methyl ethyl ketone; fatty acid amides, such as dimethyl formamide or dimethyl acetamide; sulphoxides, such as dimethyl sulphoxides; and carboxylic acid esters, such as ethyl acetate or butyl acetate. It is also sometimes advantageous to use an excess of alkylating agent as solvent.

To obtain the compounds of the formula (1) in which R represents hydrogen, the compounds containing tertiary amino groups are stirred in water or in a mixture of water and a solvent suitable for the quaternisation and treated with 1 mole of acid for each tertiary amino group to be protonised. Strong inorganic acids, such as hydrochloric or hydrobromic acid, can be used as acids. However, organic acids, such as formic acid, acetic acid, propionic acid or oxalic acid, are also suitable.

The novel compounds defined above exhibit a more or less pronounced fluorescence in the dissolved or finely divided state. They can be used for optically brightening a wide variety of synthetic, regenerated man-made or natural organic materials or substances which contain such organic materials.

Without any restriction being implied by the following classification, examples of organic materials which can be optically brightened are:

I. Synthetic materials of high molecular weight:

(a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on α,β-unsaturated carboxylic acids or derivatives of such carboxylic acids, especially on acrylic compounds, for example acrylic esters, acrylic acid, acrylonitrile, acrylic amides and their methacrylic analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, their homocondensation and co-condensation products, and aftertreatment products, for example polyesters, especially saturated polyesters (for example ethylene glycol terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyl resins), polyamides (for example hexamethylenediamine adipate), maleic resins, melamine resins, their precondensates and analogues, polycarbonates and silicones;

(d) polyaddition products, such as polyurethanes (crosslinked and uncrosslinked) and epoxide resins.

II. Regenerated man-made organic materials, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensional structures such as sheets, profiles, injection mouldings, various machined articles, chips, granules or foams, and also predominantly two-dimensional structures, such as films, foils, lacquers, coatings and impregnations or predominantly one dimensional structures, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

Fibrous materials can be, for example, in the form of endless filaments (stretched or unstretched), staple fibres, flocks, hanks, textile filament yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of brightener compounds used, it can be advantageous to carry out the treatment in a neutral or alkaline or acid bath. The treatment is usually carried out at temperatures of 20° to 140° C., for example at the boiling point of thw bath or near it (about 90° C.). Solutions or emulsions in organic solvents can also be used for the finishing according to the invention of textile substrates, as is practised in the dyeing industry in so-called solvent dyeing (pad-thermofixation application, or exhaustion dyeing processes in dyeing machines).

The fluorescent brighteners of the present invention can further be added to, or incorporated in, the materials before or during their shaping. Thus they can for example be added to the compression moulding composition or injection moulding composition during the manufacture of films, sheets (for example incorporated in polyvinyl chloride in a roller mill at elevated temperature) or mouldings.

If the fashioning of man-made synthetic or regenerated man-made organic materials is effected by spinning processes or from spinning solutions/melts, the fluorescent brighteners can be applied by the following processes:

addition to the starting substances (for example monomers) or intermediates (for example precondensates or pre-polymers), that is to say before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

The fluorescent brighteners of the present invention can, for example, also be employed in the following use forms:

(a) in mixtures with dyestuffs (shading) or pigments (coloured pigments or especially, for example, white pigments), or as an additive to dye baths, printing pastes, discharge pastes or reserve pastes, or for the aftertreatment of dyeings, prints or discharge prints;

(b) in mixtures with carriers, wetting agents, plasticisers, swelling agents, antioxidants, ultraviolet absorbers, heat stabilisers and chemical bleaching agents (chloride bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanentpress or non-iron), as well as flameproof finishes, soft handle finishes, anti-soiling finishes or antistatic finishes, or antimicrobial finishes;

(d) incorporation of the fluorescent brighteners into polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;

(e) as additives to master batches;

(f) as additives in a wide variety of industrial products in order to render these more marketable (for example improving the appearance of soaps, detergents, pigments);

(g) in combination with other optically brightening substances;

(h) in spinning bath preparations, that is to say as additives to spinning baths which are used for improving the slip for the further processing or synthetic fibres, or from a special bath before the streching of the fibre;

(i) as scintillators for various purposes of a photographic nature, for example for electrophotographic reproduction or supersensitising;

(j) depending on the substitution as laser dyes.

If the brightening process is combined with textile treatment or finishing methods, the combined treatment can in many cases advantageously be carried out with the aid of appropriate stable preparations which contain the fluorescent brightener compounds in such a concentration that the desired brightening effect is achieved.

In certain cases, the fluorescent brighteners are made fully effective by an aftertreatment. This can be, for example, a chemical treatment (for example acid treatment), a thermal treatment or a combined chemical/thermal treatment. Thus, for example, the appropriate procedure to follow in brightening a number of fibre substrates, for example polyester fibres, with the fluorescent brighteners according to the invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or combined in a single process stage.

The amount of fluorescent brightener of the present invention to be used, based on the weight of the material to be brightened, can vary within wide limits. A marked and lasting effect can be obtained even with very insignificant amounts, in certain cases 0.0001 percent by weight. But it is also possible to use amounts of up to about 0.8 percent by weight and, on occasion, up to about 2 percent by weight. For most practical purposes, it is preferable to use amounts between 0.005 and 0.5 percent by weight.

For various reasons it is often advantageous not to use the fluorescent brighteners by themselves, i.e. pure, but in admixture with a wide variety of assistants and extenders, for example anhydrous sodium sulphate, sodium sulphate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The invention is illustrated by the following Examples in which, unless otherwise stated, parts and percentages are by weight and melting and boiling points are uncorrected.

EXAMPLE 1

55 g of N-(3-diethylaminopropylamino)-N-(2'-cyanoethyl)-amine of the formula

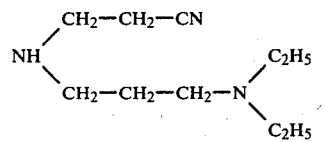

are dissolved at room temperature in 900 ml of isopropanol. With stirring, 53.3 g of the sulphochloride of the formula

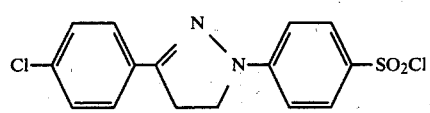

are added in the course of 1 hour. The reaction mixture is stirred for 2 hours at room temperature, heated to reflux temperature in the course of 25 minutes and refluxed for 6 hours. After cooling to room temperature, the crystallised product is collected with suction and washed with methanol. 15 g of the moist filter cake are dried in vacuo and then recrystallised twice from a mixture of 8 parts by volume of ethanol and 2 parts by volume of water, affording 6.2 g of the compound of the formula

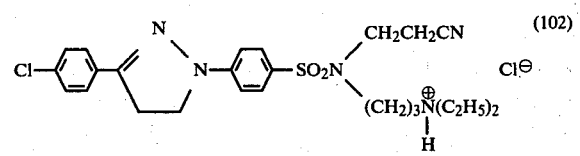

Melting point: 211°–212° C. (with decomp.).

The remainder of the moist filter cake is dissolved in 600 ml of water, and the solution is filtered clear and adjusted to pH 9 at room temperature with 20 ml of 15% sodium hydroxide solution. The precipitated product is collected with suction, dried in vacuo at 50°–60° C., and recrystallised firstly from methanol with the aid of activated carbon and then from toluene with the aid of fuller's earth, affording 31.2 g of the compound of the formula

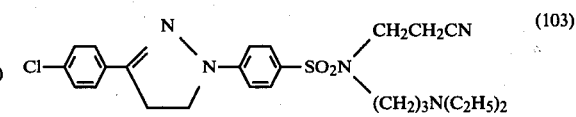

Melting point: 107°–109° C.

With stirring, 5 g of the compound of the formula (103) are dissolved in 30 ml of chlorobenzene at reflux temperature. Then 1.5 g of dimethyl sulphate are added in the course of 30 minutes and the reaction mixture is refluxed for 15 minutes, then cooled to room temperature. After decanting off the chlorobenzene, the precipitated oil is dissolved hot in 30 ml of water and the solution is filtered clear and evaporated to dryness, affording 5.3 g of an oil which crystallises slowly. Recrystallisation from methanol yields the product of the formula

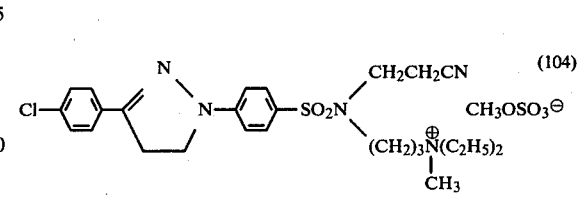

Melting point: 148°–149° C.

The compound of the formula (100) can be prepared as follows:

With stirring and cooling, 26.5 g of acrylonitrile are added dropwise to 65.1 g of 3-diethylamino-1-propylamine at 40° to 45° C. in the course of 30 minutes and the mixture is subsequently stirred for 3 hours at the same temperature. Distillation at 14 mm Hg and 148° C. yields 54.7 g of the compound of the formula (100) as a clear liquid.

EXAMPLE 2

With stirring, 53 g of the sulphochloride of the formula (101) are suspended in 360 ml of o-dichlorobenzene at room temperature. Then 24.2 g of N-(3-dimethylaminopropylamino)-N-(2′-cyanoethyl)-amine of the formula

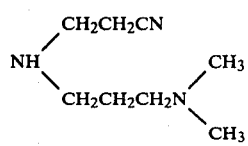

are added dropwise in the course of 30 minutes and the mixture is heated to 100° C. in the course of 40 minutes and stirred for B 2 hours at 100° to 105° C. After cooling to 90° C., 300 ml of water are added and 20 g of 30% sodium hydroxide solution are added dropwise in the course of 20 minutes. The o-dichlorobenzene is then distilled off in vacuo as an azeotrope. After cooling to room temperature, the crystallised product is collected with suction, dried in vacuo at room temperature, and recrystallized firstly from ethanol with the aid of activated carbon and then from toluene with the aid of fuller's earth and dried in vacuo at 50°-60° C., affording 36.8 g of the compound of the formula

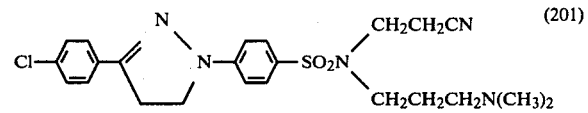

Melting point: 104°-105° C.

With stirring, 4.7 g of the compound of the formula (201) are dissolved in 30 ml of chlorobenzene at reflux temperature. Then 1.5 g of dimethyl sulphate in 4 ml of chlorobenzene are added dropwise in the course of 30 minutes, and the reaction mixture is refluxed for 10 minutes. The crystallised product is collected hot with suction, washed with two 10 ml portions of hot chlorobenzene, and dried in vacuo at 50°-60° C., affording 5.9 g of the compound of the formula

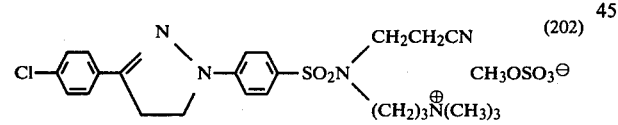

Melting point: 180°-182° C.

The amine of the formula (200) can be obtained as described in Example 1 from 3-dimethylamino-1-propylamine and acrylonitrile. Boiling point: 130°-134° C./13 mm Hg.

Using 60,8 g of the sulphochloride of the formula

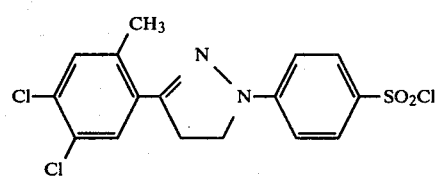

instead of the sulphochloride of the formula (101) the compound of the formula

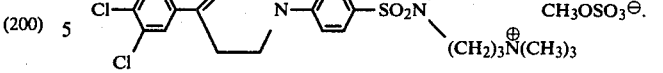

is obtained.

EXAMPLE 3

Repetition of the procedure described in Example 2 using the amine of the formula

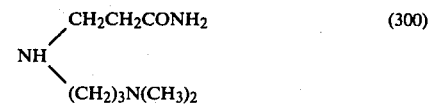

yields the compound of the formula

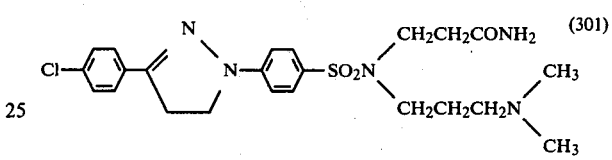

Melting point: 133°-135° C.

Quaternisation with dimethyl sulphate as described in Example 1 yields, after recrystallisation from methanol with the aid of activated carbon, the compound of the formula

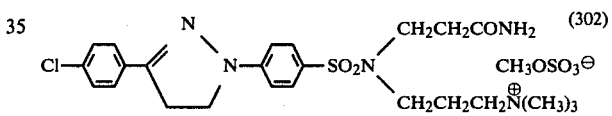

Melting point: unsharp at 77°-125° C.

The amine of the formula (300) can be obtained analogously as described in Example 1 from 3-dimethylamino-1-propylamine and acrylamide.

EXAMPLE 4

To a bath consisting of 100 ml of water, 0.1 g of oxalic acid, 0.1 g of sodium acetate, 0.025 g of trisodium phosphate, 0.06 g of octadecyl alcohol pentadecyl glycol ether and 0.0125 g of sodium bisulphite is added 0.9 ml of a solution of 1 g of the fluorescent brightening agent of the formula (102), (103), (104), (201) or (202) in 100 ml of ethylene glycol monomethyl ether at 40° C. Then a hank weighing 3 g of polyacrylonitrile yarn ("Courtelle", Courtaulds, London, England) is put into the bath, which is heated to 95° C. in the course of 10 to 15 minutes. The yarn is left for 30 minutes at 95° C. in the circulating liquor, then it is rinsed with cold water and dried.

The treated yarn has a markedly more brilliant and whiter appearance than untreated material.

EXAMPLE 5

1 g of the fluorescent brightening agent of the formula (102), (103), (104), (201) or (202) is dissolved in 1000 ml of ethylene glycol monomethyl ether, and 1.5 ml of this solution are added to 100 ml of water which contains 0.12 ml of formic acid and 0.06 g of octadecyl alcohol pentadecyl glycol ether. This fluorescent brightener solution is heated to 60° C. and then 3 g of polyacrylonitrile fabric are put into it. The temperature is raised to 95°-97° C. in the course of 10 to 15 minutes and kept for 1 hour. The fabric is then rinsed for 2 minutes in running cold water and afterwards dried for 20 minutes at 60° C. The treated fabric has a strong white effect.

EXAMPLE 6

1 g of fluorescent brightening agent of the formula (102), (103), (104), (201) or (202) is dissolved in 1000 ml of ethylene glycol monomethyl ether. Then 7.5 ml of this solution are added to 110 ml of water which contains 0.36 g of Clarit PS ® (=NaHSO₃:Na₂P₂O₇ 40%, extended) and 0.06 g of octadecyl alcohol pentadecyl glycol ether. Into this brightener solution, which is warmed to 40° C., are put 3 g of a pre-bleached woollen fabric or yarn. The temperature is raised to 60° C. in the course of 10 to 15 minutes and kept thereat for 1 hour. The fabric is then rinsed for 2 minutes in running cold water and dried for 20 minutes at 60° C. The treated fabric has a strong white effect.

EXAMPLE 7

1 g of the fluorescent brighening agent of the formula (102), (103), (104), (201) or (202) is dissolved in 1000 ml of ethylene glycol monomethyl ether. 3 ml of this solution are added to 100 ml of water which contains 0.06 g of octadecyl alcohol pentadecyl glycol ether. Into this brightener solution, which is heated to 60° C., are put 3 g of polyamide fabric (polyamide 6). The temperature is raised to 95°-97° C. in the course of 10 to 15 minutes and kept thereat for 30 minutes. The fabric is then rinsed for 2 minutes in running cold water and dried for 20 minutes at 60° C. The treated fabric has a strong white effect.

EXAMPLE 8

1 g of the fluorescent brightening agent of the formula (102), (103), (104), (201) or (202) is dissolved in 1000 ml of ethylene glycol monomethyl ether. 6 ml of this solution are added to 95 ml of water which contain 0.06 mol of acetic acid (40%) and 0.06 g of octadecyl alcohol pentadecyl glcyol ether. Into this brightener solution, which is warmed to 40° C., are put 3 g of cellulose acetate fabric. The temperature is raised to 75°-80° C. in the course of 10 to 15 minutes and kept thereat for 30 minutes. The fabric is then rinsed for 2 minutes in running cold water and dried at 60° C. The treated fabric has a strong white effect.

EXAMPLE 9

A padding liquor is prepared by dissolving 2 g of the fluorescent brightening agent of the formula (102), (103), (104), (201) or (202) and 2 g of an adduct of about 35 moles of ethylene oxide and 1 mole of octadecyl alcohol in 1000 ml of desalinated water. A woollen fabric is padded with this liquor and dried at 70° C. The treated wool has a strong white effect.

EXAMPLE 10

A padding liquor is prepared by dissolving 2 g of the fluorescent brightening agent of the formula (102), (103), (104), (201) or (202) and 2 g of an adduct of about 35 moles of ethylene oxide and 1 mole of octadecyl alcohol in 1000 ml of desalinated water. A polyamide 6 fabric is padded with this liquor and dried at 0° C. The treated fabric has a strong white effect.

EXAMPLE 11

A casting compound consisting of 10 g of polyacrylonitrile, 0.2 g of titanium dioxide (anatase modification) as matting agent and 40 ml of dimethyl formamide, and which contains 5 mg of a fluorescent brightening agent of the formula (102), (103), (104), (201) or (202), is poured onto a glass plate and drawn out to a thin film with a metal rod. After it has dried, the film has a pronounced white effect.

What is claimed is:

1. A pyrazoline derivative of the formula

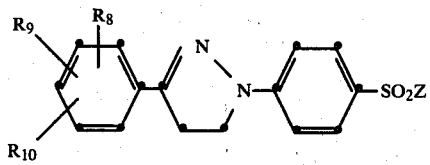

wherein $R_8$, $R_9$ and $R_{10}$, each independently of the other, represent hydrogen, halogen, lower alkyl or lower alkoxy, and Z represents a radical of the formula

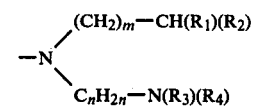

or of the formula

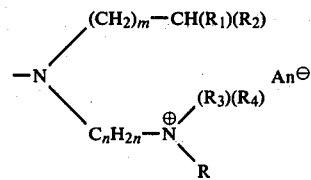

wherein $R_1$ represents a hydrogen or lower alkyl, $R_2$ represents cyano or $-CONR_6R_7$, wherein $R_6$ and $R_7$, each independently of the other, represent hydrogen or lower alkyl or together with the nitrogen atom to which they are attached, represent a saturated heterocyclic ring selected from the group consisting of pyrrolidino, piperidino and morpholino, $R_3$ and $R_4$ represent lower alkyl or together with the nitrogen atom to which they are attached represent a saturated heterocyclic ring selected from the group consisting of pyrrolidino, piperidino, morpholino and thiomorpholino, R represents hydrogen, allyl or lower alkyl, An⊖ represents $CH_3OSO_3^{\ominus}$ or $Cl^{\ominus}$, m is 0 or 1, and n is an integer from 2 to 6.

2. A pyrazoline derivative according to claim 1 of the formula

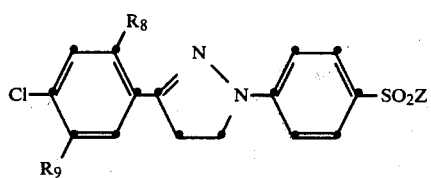

wherein
$R_8$ represents hydrogen or lower alkyl,
$R_9$ represents hydrogen or chlorine, and
Z represents a radical of the formula

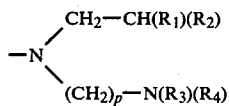

or of the formula

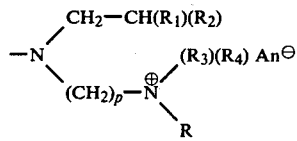

wherein
$R_1$ represents hydrogen or methyl,
$R_2$ represents cyano or $-CONR_6R_7$, wherein $R_6$ and $R_7$, each independently of the other represent hydrogen or lower alkyl,
$R_3$ and $R_4$ represent lower alkyl, and
p is 2 or 3.

3. A pyrazoline derivative according to claim 2, wherein
$R_1$, $R_8$ and $R_9$ are hydrogen,
$R_2$ is cyano or $-CONH_2$,
R is hydrogen or lower alkyl, and
p is 3.

* * * * *